United States Patent [19]

Takahara et al.

[11] Patent Number: 6,010,871
[45] Date of Patent: *Jan. 4, 2000

[54] MODIFICATION OF PEPTIDE AND PROTEIN

[75] Inventors: Yoshiyuki Takahara; Naoyuki Yamada; Masao Motoki, all of Kawasaki, Japan

[73] Assignees: Ajinomoto Co., Inc.; Drug Delivery System Institute, Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/809,593

[22] PCT Filed: Sep. 29, 1995

[86] PCT No.: PCT/JP95/01994

§ 371 Date: Sep. 8, 1997

§ 102(e) Date: Sep. 8, 1997

[87] PCT Pub. No.: WO96/10089

PCT Pub. Date: Apr. 4, 1996

[30] Foreign Application Priority Data

Sep. 29, 1994 [JP] Japan .................................. 6-270101

[51] Int. Cl.[7] .................................................. C12P 21/00
[52] U.S. Cl. ..................... 435/68.1; 424/94.5; 424/94.6; 435/193; 514/2; 530/350; 530/351
[58] Field of Search ................. 424/94.5, 94.6; 435/193; 514/2; 530/350, 351

[56] References Cited

U.S. PATENT DOCUMENTS

| | | | |
|---|---|---|---|
| 5,156,956 | 10/1992 | Motoki | 435/68.1 |
| 5,252,469 | 10/1993 | Andou | 435/71.2 |
| 5,490,980 | 2/1996 | Richardson | 424/94.6 |
| 5,514,573 | 5/1996 | Yasueda | 435/193 |
| 5,518,742 | 5/1996 | Soeda | 426/63 |
| 5,525,336 | 6/1996 | Green | 424/94.5 |
| 5,547,932 | 8/1996 | Curiel | 435/65 |
| 5,549,904 | 8/1996 | Juergensen | 424/423 |
| 5,607,849 | 3/1997 | Yasueda | 435/193 |
| 5,789,230 | 8/1998 | Cotten | 435/235.1 |

FOREIGN PATENT DOCUMENTS

| | | |
|---|---|---|
| 93/07283 | 4/1993 | WIPO . |
| 95/10624 | 4/1995 | WIPO . |

OTHER PUBLICATIONS

Ikura, Agric Biol Chem 45, 2587–2592, 1981.

Ikura, Agric. Biol. Chem. 48, 2347–54, 1984.

*Primary Examiner*—Michael P. Woodward
*Assistant Examiner*—David Lukton
*Attorney, Agent, or Firm*—Oblon, Spivak, McClelland, Maier & Neustadt, P.C.

[57] ABSTRACT

A process for modifying a physiologically active peptide or a physiologically active protein which comprises reacting a physiologically active peptide or a physiologically active protein having at least a glutamine residue with a substance having an amino donor in the presence of a transglutaminase originating in a microorganism to thereby form an acid amide bond at the γ-position acid amide group of the glutamine residue with the amino group of the amino donor; and the product of modification obtained thereby.

10 Claims, 5 Drawing Sheets

MODIFICATION OF PEPTIDE AND PROTEIN

INDUSTRIAL FIELD OF THE INVENTION

This invention relates to a process for modifying a physiologically-active peptide or protein, and to modified products of the process.

PRIOR ART

Many physiologically-active peptides and proteins are known. Hereinunder these peptides and proteins will be generically referred to as physiologically-active peptides.

Such physiologically-active peptides include, for example, peptides that physiologically act in-vivo, such as interleukin (IL)-1, -2, -3, -4, -5, -6, -7, -8, -9, -10, -11, -12, -13, -14 and -15, G-CSF, GM-CSF, M-CSF, erythropoietin, stem cell factor, mpl-ligand, $\alpha$-, $\beta$- and $\gamma$-interferons, somatostatin, vasopressin, insulin, growth hormones, Substance P, ADF (ATL-derived factor, human thioredoxin), etc.; modified peptides as produced through modification of those peptides; animal-derived peptides such as bombesin; microorganism-derived peptides such as asparaginase; and plant-derived peptides such as lysine. In addition to these, antibodies are also within the scope of such physiologically-active peptides.

Antibodies of that type include not only human monoclonal antibodies but also animal monoclonal antibodies. Some of such antibodies have been being already used in medicines and diagnostic reagents, and some others are being studied for their use in medicines and diagnostic reagents.

For example, in the field of clinical medicine, IL-2 is used in carcinostatics; erythropoietin and G-CSF are in hematinics; and insulin and growth hormones are used for treating patients who are in congenital or acquired failure in or insufficiency for these. The use of IL-6 in platelet enhancers for use in clinical medicine is being under development.

As mentioned above, physiologically-active peptides are important as medicines; and various modifications of these peptides with polymer substances and the like are being made for the purpose of imparting new functions to the peptides and for the purpose of compensating for lack of safe usability of the peptides in medicine.

For example, a congenital immune disorder, adenosine deaminase insufficiency is caused by the insufficiency for normal adenosine deaminase (ADA), for which is used a medicine comprising polyethylene glycol (PEG)-modified ADA for the purpose of prolonging the in-vivo retention time for ADA.

On the other hand, for many of physiologically-active peptides, it is indispensable to specifically bond to the corresponding receptors or ligands in order to exhibit their physiological functions; and on the basis of the specific bonding of that type, it may be possible to utilize specific physiologically-active peptides as targeting molecules.

For example, a proposal has been made for bonding diphtherotoxin to IL-6 molecules and delivering the thus-bonded diphtherotoxin specifically to cancer cells having IL-6 receptors thereby to kill the cancer cells. Apart from this, a method has been developed for bonding a carcinostatic to a monoclonal antibody capable of recognizing a cancer-specific antigen, followed by delivering the thus-bonded carcinostatic specifically to cancer cells. It is said that the method will be also effective for killing cancer cells.

In addition, means of utilizing physiologically-active peptides in drug delivery systems (DDS) are important even in the field of genetic treatment. In particular, great expectations are put on the in-vivo administration of genes for genetic treatment. For example, George Y. Wu et al. have developed a method of genetic treatment in which a polylysine (this is charged positively) are chemically bonded to a physiologically-active peptide, such as orosomucoid, then a DNA plasmid (this is charged negatively) is enveloped in the resulting composite, and the thus-enveloped DNA is delivered to liver cells having orosomucoid receptors (see J. Biol. Chem., 263, 14621, 1988).

The problems on the use of physiologically-active peptides in clinical medicine are mentioned below.

1. Side Effects:

It may be believed that, even when physiologically-active peptides, which physiologically act in-vivo by nature, they will exhibit no side effects in-vivo, but, in actual administration of such physiologically-active peptides to living bodies in the site of clinical medicine, almost all physiologically-active peptides exhibit some side effects in-vivo. This is because physiologically-active peptides are naturally produced in local sites in-vivo, released and acts on the local sites, and thereafter most of those are decomposed in situ. However, a physiologically-active peptide as administered to a patient is distributed throughout its body to temporarily increase the concentration of the peptide in blood, whereby it generally involves any non-physiological reaction or medically-undesirable reaction 2. Rapid Metabolism Speed:

For many exogenous peptides including even physiologically-active ones, their presence in-vivo for a long period of time is undesirable for living bodies. Therefore, most exogenous peptides administered to living bodies are soon decomposed in blood, or, after having been caught in some organs, they are then decomposed therein. Thus, those exogenous peptides rapidly disappear from blood. However, such behavior of exogenous peptides is a bar to the exhibition of the pharmaceutical potency of physiologically-active peptides when the peptides are administered to patients.

3. Antigenicity:

Physiologically-active peptides originally existing in-vivo by nature has low antigenicity, while artificial physiologically-active peptides as produced through genetic recombination are different from such natural ones, for example, including those lacking in glyco-chains and those having additional glyco-chains that are different from those existing in natural ones. Such recombinant peptides are used in clinical medicine, but they often have significant antigenicity. Therefore, when such recombinant physiologically-active peptides are administered to patients continuously of frequently for a long period of time, antibodies corresponding to the peptides are formed in-vivo in the patients. In those cases, the antibodies thus produced neutralize the physiologically-active peptides as administered to the patients, resulting in that the peptides could no more exhibit their potency and that, if the worst comes to the worst, the peptides will often induce some allergic reactions that are harmful to human bodies.

In order to solve the above-mentioned problems with physiologically-active peptides, the following measures maybe taken.

1. Molecules having specific affinity for organs or tissues, for example, molecules as prepared by bonding IL-6 molecules to a stem cell factor (SCF) capable of specifically bonding to the c-kit molecules that broadly exist in marrow cells, IL-6/SCF molecules are concentrated in the marrow, in which said IL-6/SCF molecules can exhibit the action of IL-6 to promote the differentiation of megakaryocytes into platelets, thereby increasing the number of platelets. IL-6 acts on the hypothalamus, thereby inducing fever via the central nervous system, but the concentration of IL-6 in the marrow will reduce its side effect to induce fever.

Similarly, in order to make IL-2 act specifically on tumor-specific cytotoxic T cells (CTL), IL-2 molecules as bonded to tumor antigen molecules, to tumors themselves, or to fractions fractionated from debris of disrupted tumor cells may be administered to patients. In those cases, the CTL cells capable of recognizing the tumor antigen bond to the tumor antigen, and thus are effectively activated by IL-2 as bonding to the antigen. Then, the thus-activated CTL cells could attack the tumor cells.

For interferons (α-, β-, γ-IFN) that are used for treatment of viral hepatitis, a ligand for a liver asialoglycoprotein receptor, such as asialoglycoprotein or the like, may be bonded to these in order that the thus-bonded IFNs may be targeted to the liver to thereby reduce the side effects of IFNs.

For TNF, G-CSF, GM-CSF, IL-11, SCF, mpl-ligand, LIF, IL-3 and the like that are used for making them act on precursor cells in hematopoietic systems to thereby differentiate and propagate the cells, or are used for making them act on hematopoietic cancers to thereby enhance the action of immune systems or carcinostatics, they may be bonded to the corresponding acting cells or to the molecules (targeting molecules) having the ability to bond to the supporting cells adjacent to the acting cells, and the thus-bonded composites may be used to thereby reduce the side effects of said substances. The same may apply also to TNF and IFN that are used for the treatment of cancers other than those in hematopoietic systems.

2. IL-6 as administered to patients rapidly disappear from their blood. However, if IL-6 is bonded to polymer substances that are hardly trapped in in-vivo reticuloendothelial systems (RES), such as human serum albumin (HSA), polylysine and PEG, the half-value life of IL-6 in blood could be prolonged.

ADF (ATL derived factor, human thioredoxin; see Mitsui et al., (1992) Biophys. Biochem. Res. Com. 186 (3), 1220–1226) and SOD (superoxide dismutase) are in-vivo molecules capable of reducing nascent-state oxygen, and their use in clinical medicine as anti-inflammatory agents is being attempted. For this, if the intended ADF or SOD concentration in blood could be maintained for a long period of time, a higher anti-inflammatory effect of the substance could be attained. Like IL-2, ADF or SOD can be bonded to HSA or PEG, thereby enhancing the anti-inflammatory effect of said ADF or SOD.

The same as above may apply also to IL-2, IFN, G-CSF, GM-CSF, IL-11, SCF, mpl-ligand, LIF, IL-3, TNF and the like to thereby increase their effects.

3. Various types of genetic diseases are known, which are caused by the congenital failure in some types of enzymes. For example, the failure in purine nucleoside phosphorylase (PNP) results in neuropathy to death, which, however, could be prevented in some degree if bovine PNP with polyethylene glycol (PEG) bonded thereto is administered to the patients.

The bonding of PEG to bovine PNP reduces the antigenicity of said bovine PNP, which has made it possible to use bovine PNP in clinical medicine. This is considered because the site of bovine PNP to cause its antigenicity is masked with PEG. Similarly, it is expected that the bonding of HSA to PNP will also reduce the antigenicity of PNP.

For snake venom peptides that are used for the treatment of thromboses, the same antigenicity-reducing effects as in the above may be obtained if HSA or PEG is bonded to said peptides.

As has been mentioned hereinabove, both for the modifications for removing the problems with physiologically-active peptides and for the use of physiologically-active peptides as targeting molecules, it is important to modify such physiologically-active peptides by bonding thereto any of other physiologically-active peptides, glyco-chains, PEG and others without losing the individual functions. In general, chemical methods are employed for the bonding to attain such modifications. However, in chemical reactions, it is difficult to control the sites at which the intended chemical bondings is formed and to control the number of the chemical bondings to be formed, and it is also difficult to obtain bonded products still having the activities of the both parties as bonded. For use in medicines, it is extremely important to constantly produce bonded products having the same structure, but it is difficult to control the production line for that purpose. In particular, where polymers are bonded to each other, a plurality of different types of bonded products are produced at the same time, and it is extremely difficult to isolate and purify the intended single product from them.

DISCLOSURE OF THE INVENTION

The present invention relates to a process for modifying a physiologically-active peptide or protein, which comprises reacting a physiologically-active peptide or protein having at least a glutamine residue with a substance having an amino donor in the presence of a microorganism-derived transglutaminase to thereby form an acid amido bond at the γ-positioned acid amido group of the glutamine residue with the amino group of the amino donor.

The invention also relates to a modified, physiologically-active peptide or protein as produced according to a process for modifying a physiologically-active peptide or protein, the process comprising reacting a physiologically-active peptide or protein having at least a glutamine residue with a substance having an amino donor in the presence of a microorganism-derived transglutaminase to thereby form an acid amido bond at the γ-positioned acid amido group of the glutamine residue with the amino group of the amino donor.

We, the present inventors have assiduously studied in order to solve the above-mentioned problems, and, as a result, have found that a substance having an amino donor (amino group) can be selectively bonded to a physiologically-active peptide or protein under mild conditions if a transglutaminase is used for the bonding.

Transglutaminase (EC 2.3.2.13) (genealogical name: protein-glutamine:γ-glutamyltransferase is a known enzyme that catalyzes the specific bonding of the glutamine residue in a peptide or protein to the amino group in an amino group-having substance. Various transglutaminases are disclosed in many reports, some of which are mentioned below.

(a) J. E. Folk et al., Adv. Protein Chem., 31, 1–133, 1977
(b) J. E. Folk et al., Adv. Enzymol., 38, 109–191, 1973
(c) H. Bohn et al., Mol. Cell Biochem., 20, 67–75, 1978
(d) L. Lorand et al., Handbook of Biochemistry and Molecular Biology, Vol. 2, Proteins, ed. G. D. Fasman, pp. 669–685, Cleveland: CRC, 3rd ed.
(e) Guinea Pig and Rabbit Liver Transglutaminase: T. Abe et al., Biochemistry, 16, 5495–5501 (1977)
(f) Human Red Blood Cells Transglutaminase: S. C. Brenner et al., Biochim. Biophys. Acta.522, 74–83, 1978
(g) Rat Coagulating Gland Transglutaminase: J. Wilson et al., Fed. Proc., 38, 1809 (Abstr.), (1979)

Depending on their origins, various types of transglutaminases are known. For example, known are microorganism-derived transglutaminases (e.g., bacterial transglutaminase—hereinafter referred to as BTG—this is reported for example in H. Ando et al., Agric. Biol. Chem., 53 (10), 2613–2617 (1989); K. Washizu et al., Biosci. Biotech. Biochem., 58 (1), 82–87 (1994)); and animal-derived transglutaminases (mammalian transglutaminases) such as liver transglutaminase, plasma factor XIIIa, platelet and placental factor XIIIa, hair-follicle transglutaminase, epidermal transglutaminase, prostate transglutaminase, etc. Any of these can be used in the present invention, but BTG is preferred herein.

The bonding reaction to be effected in the presence of transglutaminase is limited to the specific site, and therefore this reaction is advantageous in that it produces few side products and that it is easily controlled. In addition, since the reaction is an enzymatic reaction, it is superior to chemical reactions in the following points.

i) There is a large possibility that the individual substances to be bonded can be bonded to each other only at the specific site to form a bonded product without losing the original functions of the individual substances bonded.

ii) Since the conditions for the bonding reaction are physiological conditions, the individual substances to be bonded are not denatured.

iii) Since the quality of the bonded products can be kept constant, high-quality medicines can be produced.

On the other hand, for protein-to-protein bonding, known is a method of using recombinant DNA technology in which different genes are bonded to each other. Over the recombinant DNA method of that type, the process of this invention of utilizing transglutaminase is advantageous in the following points.

i) In the transglutaminase-using enzymatic process, being different from the recombinant DNA method, it is possible to bond to peptides or proteins, any substances that could not be directly obtained from DNA, such as glyco-chains, glyco-proteins, glyco-lipids, PEG and others.

ii) In the recombinant DNA method, only fused proteins can be formed in which another protein is bonded to the N-terminal or C-terminal of a protein.

iii) As mentioned above, in the recombinant DNA method, only fused proteins can be formed in which another protein is bonded to the N-terminal or C-terminal of a protein. Therefore, in this, if the latter protein has its activity center at its terminal, there is a great possibility that the resulting fused protein will lose the activity.

As opposed to this, in the process of the invention using transglutaminase, the substance having an amino group can be bonded specifically to only the acid amido group of the glutamine residue in the peptide or protein. In this, therefore, bonded products that are different from those to be obtained in the recombinant DNA method can be obtained. In the process of the invention, since the bonding is controlled by the action of BTG, the bonded product can exhibit the activities of the two compounds as bonded.

According to the process of this invention, a substance having an amino donor can be bonded to a physiologically-active peptide or protein through the enzymatic reaction of the two to be effected in the presence of transglutaminase under the conditions for the enzymatic reaction with the transglutaminase used.

For example, when BTG is used, the two can be reacted at a temperature falling between 4° C. and 55° C., preferably between 30° C. and 50° C., and at a pH falling between 5 and 8, preferably between 6 and 7.5.

One example of measuring transglutaminase activity is referred to hereinunder.

The activity unit of transglutaminase to be used herein may be measured in the manner mentioned below. Briefly, transglutaminase is reacted on a reaction system comprising substrates of benzyloxycarbonyl-L-glutamine-glycine and hydroxylamine in a tris buffer at a temperature of 37° C. and at a pH of 6.0, in the presence of 5 mM $Ca^{2+}$ for the animal-derived transglutaminase but in the absence of the same for the microorganism-derived transglutaminase; then the thus-formed hydroxamic acid is formed into its iron complex in the presence of trifluoroacetic acid; and the absorbance at 525 nm of the resulting complex is measured; the amount f the hydroxamic acid formed is obtained from the calibration curve; and the amount of the enzyme, transglutaminase to produce 1 $\mu$mol of hydroxamic acid for 1 minute is obtained to be the activity of the enzyme, 1 unit (1 U).

The substance having an amino acid donor for use in the process of the present invention to modify a physiologically-active peptide is not specifically defined, provided that it has an amino group in the molecule, but is preferably a peptide or protein having an amino group. Preferred examples of the substance include physiologically-active peptides and proteins such as those mentioned hereinabove; antibodies, especially monoclonal antibodies; antigens; and alkylamine derivatives of polyamino acids and those of polyethylene glycol, especially alkylamine derivatives of polylysine or polyethylene glycol. These preferred substances may have a molecular weight of from 3,000 to 200,000, preferably from 3,000 to 100,000, more preferably from 5,000 to 200,000, even more preferably from 10,000 to 100,000.

The physiologically-active peptide to be modified according to the process of the present invention is not specifically defined, provided that it has glutamine in its amino acid sequence, but is preferably any of physiologically-active peptides and proteins such as those mentioned hereinabove, more preferably any of interleukin-2, interleukin-6, interferons, ADF( ATL derived factor, human thioredoxin) and the like.

Examples of modified products of physiologically-active peptides or proteins to be obtained according to the process of the present invention are mentioned below.

1) There is a possibility that IL-2 acts on immunoreaction-participating cells to enhance the immunity of the cells, thereby killing cancer cells. However, if IL-2 is systemically administered to patients, it exhibits severe side effects. Therefore, it is said that it is important to make IL-2 focus only on the sites on which it shall act, or that is on T cells or NK/LAK cells, or to make it focus only on the sites around cancer cells.

Examples of modified IL-2 are as follows:

IL-2/anti-CD8 antibody [This focuses on CD8-positive T cells.]

IL-2/anti-CD4 antibody [This focuses on CD4-positive T cells.]

IL-2/anti-NK/LAK cell antibody [This focuses on NK/LAK cells.]

IL-2/antibody to hepatocyte-specific antigen (e.g., anti-sulfide antibody, anti-albumin receptor antibody) [This focuses on the liver to enhance the immunity of the sites around hepatoma.]

IL-2/poly-HSA [Since poly-HSA bonds to the albumin receptor antibody in the liver, this IL-2/poly-HSA focuses on hepatoma.]

IL-2/anti-ErbB2 antibody or ErbB2 ligand [This focuses on cancers having ErbB2.]

IL-2/antibody to colon cancer-specific cancer antigen [This focuses on colon cancer.]

IL-2/antibody to melanoma-specific cancer antigen [This focuses on melanoma.]

IL-2/polylysine [Its half-value period in blood is prolonged.]

IL-2/PEG (polyethylene glycol) [Its half-value period in blood is prolonged.]

IL-2/HSA (human serum albumin) [Its half-value period in blood is prolonged.]

IL-2 dimer [Its half-valueperiodinbloodis prolonged.]

IL-2/lentinan [This exhibits enhanced, synergistic carcinostatic effects.]

IL-2/IL-9 [This exhibits synergistic effects for activating T-cells.]

IL-2/IL-12 [This exhibits synergistic effects for activating T-cells.]

IL-2/toxin (e.g., tetanus toxin, Pseudomonas toxin) [This removes cancer cells having IL-2 receptors.]

2) IL-6 acts on precursor cells of platelets to increase the number of platelets, but also acts on the liver to release acute-stage proteins and acts on central nervous systems to induce fever. Therefore, it is said that, if this is used as a platelet-enhancing agent, it is important to make IL-6 focus only on the marrow. When the concentration of IL-6 in blood is larger than a predetermined value, IL-6 exhibits some side effects. However, it is believed that, if the half-value period of IL-6 in blood could be prolonged, the administration of IL-6 that may cause temporary increase in the concentration of IL-6 in blood could be prevented. Therefore, if the half-value period of IL-6 in blood is prolonged to attain the slow release of IL-1 into blood, the side effects of IL-6 could be reduced.

Examples of modified IL-6 are as follows:

IL-6/antibody to marrow cells or supporting cells for marrow cells (e.g., stroma cells, etc.) [This focuses on the marrow.]

IL-6/ligand to receptors that are much expressed in marrow cells (e.g., SCF, IL-11, mpl-ligand, G-CSF, GM-CSF, or IL-3) [This focuses on the marrow. Especially, IL-6/SCF and IL-6/mpl-ligand exhibit synergistic effects for enhancing their platelet-increasing effect and hematopoietic stem cell-increasing effect.]

IL-6/ligand to marrow cell-specific extracellular matrices, or molecule having specific affinity for said matrices [This focuses on the marrow.]

IL-6/polylysine [Its half-value period in blood is prolonged.]

IL-6/PEG [Its half-value period in blood is prolonged.]

IL-6/HSA [Its half-value period in blood is prolonged.]

IL-6dimer [Its half-value period in blood is prolonged.]

IL-6/toxin (e.g., tetanus toxin, Pseudomonas toxin) [This removes cancer cells having IL-6 receptors, for example, removes myeloma.]

3) In addition, IL-6 participates in autoimmune diseases, such as rheumatoid arthritis, Castlemann's disease, etc., and often causes some diseases or is often an exacerbating factor for some diseases, for example, inducing hyper-propagation of leukemia cells due to hyper-expression of IL-6 and IL-6 receptors, or causing dyscrasia in some types of cancer cells, or inducing shock in bacterial infection. Therefore, an anti-IL-6 antibody and an anti-IL-6 receptor antibody to remove the effects of IL-6 may be medicines for the above-mentioned disorders.

The use of an anti-IL-6 antibody in the treatment of rheumatoid arthritis is referred to. An anti-IL-6 antibody is a mouse monoclonal antibody. The antibody may be directly used as it is; or after the variable region of the antibody is fused to the constant region of a human antibody to give a chimera antibody or a single-stranded antibody of a fused protein composed of an L-chain (light chain) variable region and an H-chain (heavy chain) variable region, and the resulting chimera antibody or single-stranded antibody is used. Any type of the original antibody or the modified antibodies is administered to joint cavities. Anyhow, the human body to which any of the antibodies has been administered produces in itself an antibody to the administered antibody. In that case, there is a probability that the effects of the anti-IL-6 antibody will be dismissed in the human body. In addition, for the artificial single-stranded antibody, there is a probability that the half-life period of the antibody in blood and in joint cavities will be short.

For these reasons, the reduction in the antigenicity of the anti-IL-6 antibody and the prolongation of the half-life period of said antibody in blood or in joint cavities are effective in use of said antibody.

For a bifunctional antibody (BFA) as prepared by bonding two different antibodies to each other, one having one specificity while the other having another one specificity that is different from the specificity of the former, there is a possibility that the BFA may be a new medicine. For example, a BFA comprising an anti-IL-6 antibody and an anti-IL-1 antibody as bonded to each other could exhibit synergistic effects while inhibiting both IL-1 and IL-6 that are the exacerbating factors for rheumatoid arthritis.

Examples of modified anti-IL-6 antibodies are mentioned below.

Anti-IL-6 antibody/HSA [Its half-life period in blood and in joint cavities is prolonged, and its antigenicity is reduced.]

Anti-IL-6 antibody/polylysine [Its half-life period in blood and in joint cavities is prolonged, and its antigenicity is reduced.]

Anti-IL-6 antibody/collagen [Its half-life period in blood and in joint cavities is prolonged, and its antigenicity is reduced.]

Anti-IL-6 antibody/anti-IL-1 antibody [Its effect for curing rheumatoid arthritis is enhanced.]

4) Polylysine is a polymer having positive charges, and this envelops and protects DNA molecules having negative charges in aqueous solutions. Targeting molecules are bonded to such polylysine, and the thus-bonded product is mixed with DNA molecules to form a composite where the DNA is enveloped in the targeting molecules. Where this composite is in-vivo administered, the gene can be specifically introduced into the tissue that corresponds to the targeting molecules in which the gene can express the intended protein. The molecules to envelop the DNA are not always limited to those of polylysine, but any and every substance which has some affinity for the DNA, which is harmless to living bodies and which is hardly trapped in some sites in circulation systems may be used for that purpose.

5) INF-α, -β, and -γ have anti-viral activities and are used for the treatment of viral hepatitis. However, administration of large amounts of these and continuous administration of these cause serious side effects. Therefore, if they are targeted to only the sites on which they shall act, for example, to the liver, the side effects of these INFs could be reduced. In that case, a ligand corresponding to the asialoglycoprotein receptor existing on the surfaces of liver parenchyma cells may be bonded to the INF, whereby the thus-bonded INF can be targeted to the liver. On the other hand, in order to prevent the temporary increase in the concentration of INF in blood, some measures shall be taken such that the half-life period of INF in blood is prolonged while INF is released slowly into blood, whereby the side effects of INF may be reduced.

Examples of modified INFs are mentioned below.

INF/asialo-orosomucoid [This focuses on the liver.]

INF/asialofetuin [This focuses on the liver.]

INF/galactose-modified albumin [This focuses on the liver.]

INF/galactose-modified polylysine [This focuses on the liver.]

INF/branched galactose synthetic ligand [This focuses on the liver.]

INF/PEG [Its half-life period in blood is prolonged.]

INF/polylysine [Its half-life period in blood is prolonged.]

INF/HSA [Its half-life period in blood is prolonged.]

INF dimer [Its half-life period in blood is prolonged.]

6) Since ADF (ATL derived factor) reduces nascent-state oxygen, its use as an anti-inflammatory agent in clinical medicine is being attempted. However, the retentiveness of ADF in blood is poor. Therefore, if the half-life period of ADF in blood is prolonged, the anti-inflammatory activity of ADF can be enhanced. In addition, it is expected that ADF may be applied to the treatment of hepatocytic mitochondrial function failure in liver tissue disorders. Therefore, the targeting of ADF to the liver is helpful in enhancing the effect of ADF.

Examples of modified ADF are mentioned below.

ADF/PEG [Its half-life period in blood is prolonged.]

ADF/polylysine [Its half-life period in blood is prolonged.]

ADF/HSA [Its half-life period in blood is prolonged.]

ADF dimer [Its half-life period in blood is prolonged.]

ADF/asialo-orosomucoid [This focuses on the liver.]

ADF/asialofetuin [This focuses on the liver.]

ADF/galactose-modified albumin [This focuses on the liver.]

ADF/galactose-modified polylysine [This focuses on the liver.]

ADF/branched galactose synthetic ligand [This focuses on the liver.]

According to the present invention in which is used a microorganism-derived transglutaminase (e.g., BTG), a physiologically-active peptide or protein having glutamine can be modified specifically at its glutamine residue under mild conditions. The modification brings about improvements in the properties of the thus-modified peptide or protein without removing the intrinsic characteristics of the original physiologically-active peptide or protein. According to the present invention, since such a physiologically-active peptide or protein having glutamine can be fused specifically to a different peptide or protein having an amino group under mild conditions, it is possible to obtain useful fused proteins having both the intrinsic characteristics of the individual peptides or proteins. For example, when a physiologically-active peptide or protein is modified with an antibody, especially with a monoclonal antibody, the thus-modified peptide or protein can focus specifically on the desired sites, such as tissues, organs and cells that require said physiologically-active peptide or protein.

MODES OF CARRYING OUT THE INVENTION

Now, the present invention is described concretely on the basis of its examples, which, however, are not intended to restrict the scope of the invention.

EXAMPLE 1

Search for Various Physiologically-active Proteins to be Substrates for BTG:

Physiologically-active proteins, recombinant human (rh) IL-2, rhIL-6 and HSA, which are mentioned below, were tested herein.

rhIL-2: 1 mg/ml, 70 mM sodiumacetate, pH 5.0, 250 mM NaCl rhIL-6: 1.75 mg/ml, 10 mM sodium citrate, pH 6.0

HSA: producedby Pasteur Merieux (soldby Fuji Revio), 200 mg/ml

Method:

1) To 1 ml of a solution containing from 0.5 to 2 mg of each protein sample, added was the same amount of a solution of 50 $\mu$M monodansylcadaverine (pH 7.5, 50 mM Tris-HCl). A minimum indispensable amount of 0.1 N NaOH was added thereto, whereby the pH of each solution was adjusted to fall between 7.2 and 7.4.

2) 10 $\mu$l of a solution of pure BTG (10 units/ml) was added to 250 $\mu$l of each solution prepared in the above, and incubated therein at 37° C. for 2 hours by static culture. Then, 20 $\mu$l of 1 M ammonium sulfate was added thereto to stop the reaction. As the control, prepared was a sample to which was added the ammonium sulfate solution prior to the addition thereto of the enzyme liquid.

3) 200 $\mu$l of the thus-reacted solution was sampled in a 96-well micro-well plate (produced by Nunc), and its fluorescent intensity was measured using a fluorescent plate reader (Cytofluor, produced by Millipore). In this device, the filter was for excitation of 360/40 nm and for emission of 530/25 nm. and the sensitivity of 6 was selected.

Results:

The results obtained are shown in Table 1.

TABLE 1

| | Fluorescent Intensity | | |
|---|---|---|---|
| Protein | Control | BTG-Processed Sample | Reactivity with BTG |
| rhIL-2 | 523 | 597 | + |
| rhIL-6 | 550 | 2,267 | + |
| HSA | 695 | 940 | + |

EXAMPLE 2

Crosslinking Polymerization of rhIL-2 and rhIL-6 with BTG:

Reagents:

The same solutions of rhIL-2 and rhIL-6 as those in Example 1 were used.

Method:

1) 10 µl of the same enzyme solution as that used in Example 1 was added to 100 µl of the rhIL-2 or rhIL-6 solution, and left at 37° C. for 90 minutes. To the control, added was the same amount of distilled water in place of the enzyme solution. Immediately after the reaction, 100 µl of a liquid reagent for SDS-PAGE was added to each reaction solution to prepare a sample for SDS-PAGE.

2) Using Phast System, the sample was subjected to SDS-PAGE, in which Phast Gel 10–15 was used as the gel. The sample was stained using Phast Silver Stain Kit. The amount of the sample tested herein was 1 µl.

Figure 1:
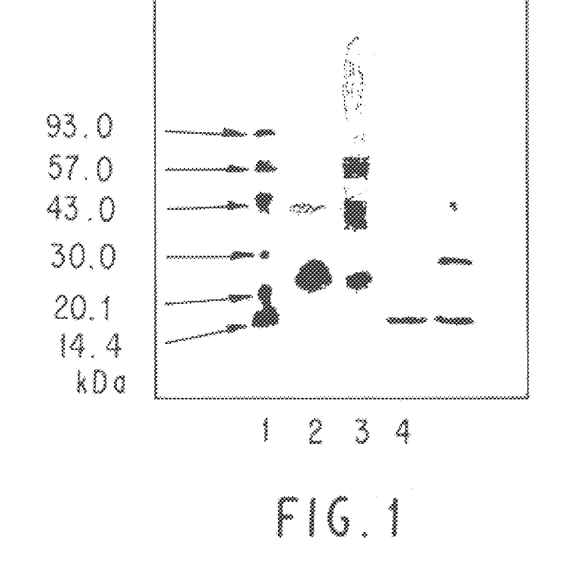
FIG. 1 shows the SDS-PAGE patterns of BTG-processed IL-6 and IL-2.
Figure 2A:
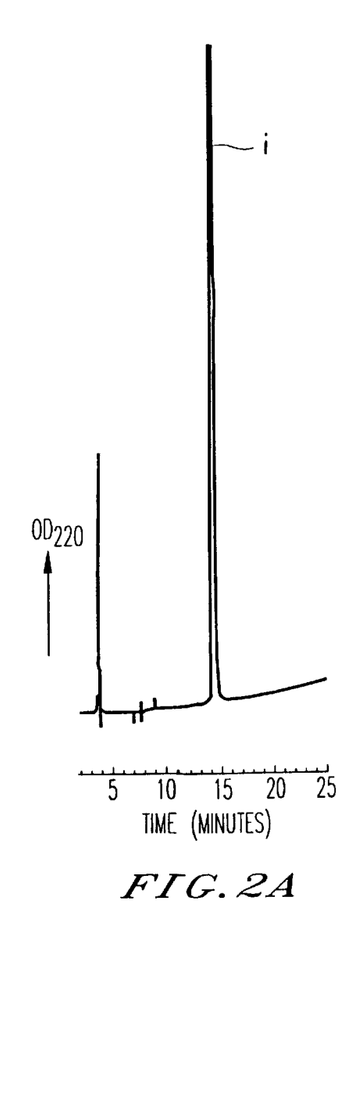
FIG. 2 shows the chromatography patterns of pure polylysine-bonded IL-6.
Figure 2B:
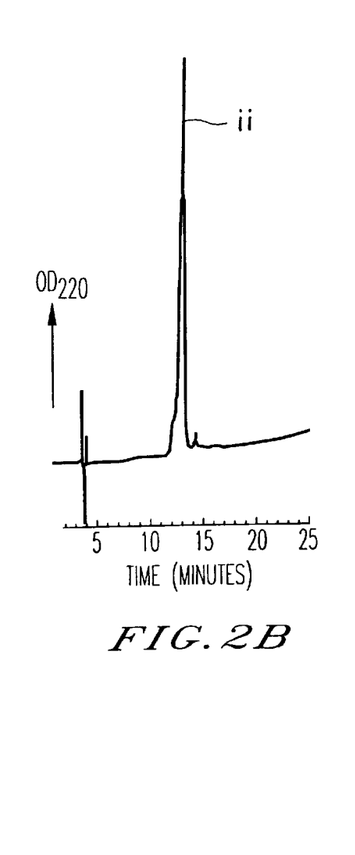
Figure 2C:
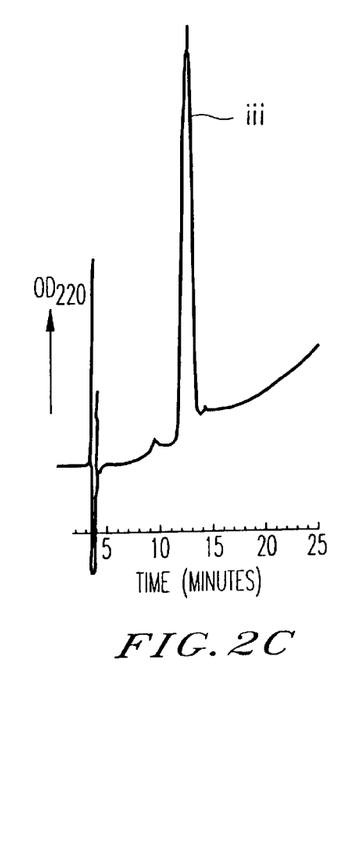
Figure 2D:
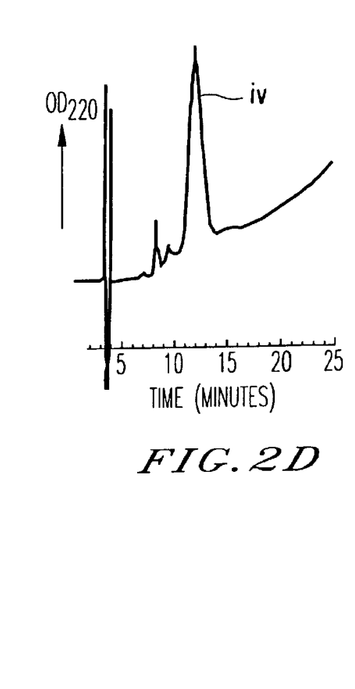

The SDS-PAGE patterns are shown in FIG. 1, in which 1 indicates the marker, 2 indicates rhIL-6, 3 indicates BTG-processed rhIL-6, 4 indicates rhIL-2, and 5 indicates BTG-processed rhIL-2.

BTG-processed 3 and 5 gave polymer spots, from which it is known that rhIL-2 and rhIL-6 are crosslinked and polymerized through the processing with BTG.

EXAMPLE 3

Preparation of Polylysine-Bonded rhIL-6:

10 mg of polylysine hydrobromide (molecular weight: 7,900, 45,700 or 83,800—produced by Sigma) was dissolved in 1 ml of 50 mM Tris-HCl (pH 7.5). To this was added 50 µl of a solution of BTG (14 U/ml, 50 mM Tris-HCl, pH 7.5), and incubated at room temperature for 30 minutes. Next, 2 ml of a solution of rhIL-6 (2 mg/ml, 10 mM sodium citrate, pH 6.0) was added thereto, stirred, and left at 37° C. for 2.5 hours (for the polymer having a molecular weight of 7,900) or for 20 hours (for the polymer having a molecular weight of 45,700 or 83,800). Then, the reaction solution was purified through reversed-phase HPLC.

The conditions for the elution in this reversed-phase HPLC were the same as those for that in the reversed-phase HPLC that gave the patterns of FIG. 2. The polylysine-bonded IL-6 fractions were collected and concentrated through reversed-phase HPLC, for which the conditions were the same as those for FIG. 2. In this, however, the time for the elution of from 0% of B to 100% of B was 5 minutes. The polylysine-bonded rhIL-6 fractions were collected and subjected to gel permeation to remove the solvent.

The conditions for the gel permeation were as follows:

Column: Sephadex G-25 (1×10 cm)

Buffer: 20 mM Tris-HCl, 0.5 M NaCl, pH 8.5

Flow Rate: 2 ml/min

The thus-purified, polylysine-bonded rhIL-6 was analyzed through reversed-phase HPLC, and the data obtained are shown in FIG. 2. As in FIG. 2, the bonded product was almost completely purified to be a single substance.

In FIG. 2;

1 indicates rhIL-6 (retention time: 14.12 min);

2 indicates rhIL-6 with polylysine having a molecular weight of 7,900 bonded thereto (retention time: 12.38 min);

3 indicates rhIL-6 with polylysine having a molecular of 45, 700 bonded thereto (retention time: 12.16 min); and 4 indicates rhIL-6 with polylysine having a molecular weight of 83, 800 bonded thereto (retention time: 11.46 min)

The conditions for the HPLC were as follows:

Column: Vydac Protein C4 214TP54 (4.6×250 mm)

Solvents: 0.1% trifluoroacetic acid (TFA) for A 0.1% TFA—80% acetonitrile for B

Elution Program: 20 minutes from 40% of B to 100% of B

Flow Rate: 1 ml/min

Figure 3:
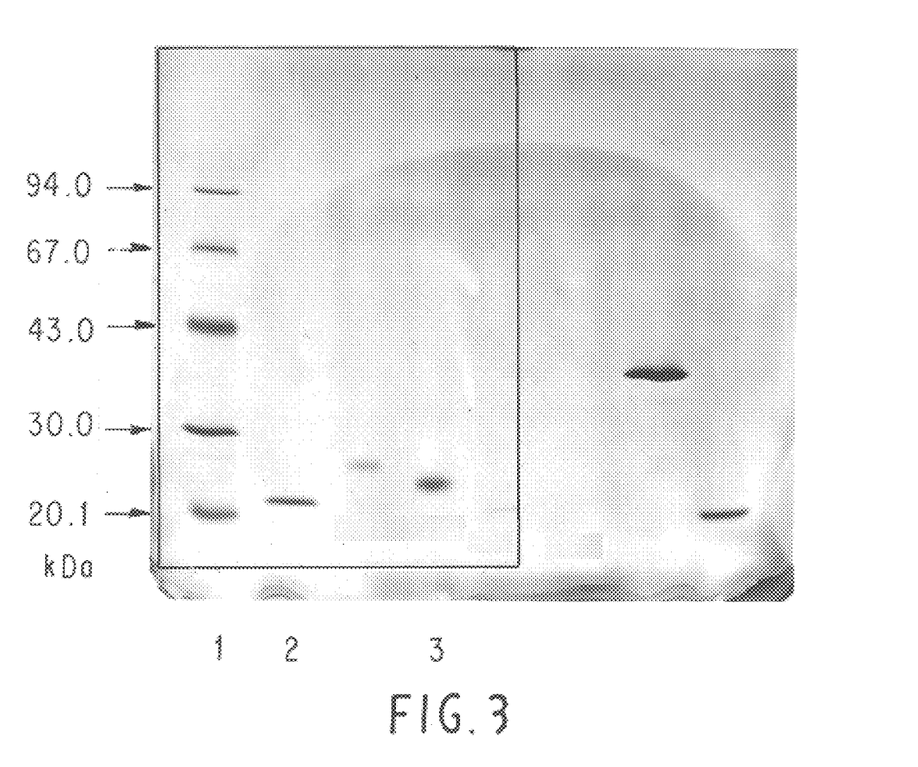
FIG. 3 shows the SDS-PAGE patterns of polylysine-bonded rhIL-6.

FIG. 3 shows the SDS-PAGE patterns of the polylysine-bonded rhIL-6 (where the polymer had a molecular weight of 7,900). As in FIG. 3, the polylysine-bonded rhIL-6 gave a single band.

In FIG. 3, 1 indicates the marker, 2 indicates rhIL-6, and 3 indicates the polylysine-bonded rhIL-6 (where the polymer had a molecular weight of 7,900).

EXAMPLE 4

Preparation of Polyethylene Glycol (PEG)-Bonded rhIL-6:

10 mg of bis(6-aminohexyl) polyoxyethylene (molecular weight: 3,350—produced by Sigma) was dissolved in 1 ml of 50 mM Tris-HCl (pH 7.5). To this was added 50 µl of a solution of BTG (14 U/ml, 50 mM Tris-HCl, pH 7.5), and left at room temperature for 30 minutes. Next, 2 ml of a solution of rhIL-6 (2 mg/ml, 10 mM sodium citrate, pH 6.0) was added thereto, stirred, and left at 37° C. for 2.5 hours. Then, the reaction solution was purified through reversed-phase HPLC. The conditions for this reversed-phase HPLC were the same as those in Example 3 (for FIG. 2). The PEG-bonded rhIL-6 fractions were collected and concentrated through reversed-phase HPLC, for which the conditions were the same as those in Example 3. In this, however, the time for the elution program of from 0% of B to 100% of B was 5 minutes. The PEG-bonded rhIL-6 fractions were collected and subjected to gel permeation for de-salting.

The conditions for the gel permeation were as follows:

Column: Sephadex G-25 (1×10 cm)

Buffer: 20 mM Tris-HCl, 0.5 M NaCl, pH 8.5

Flow Rate: 2 ml/min

Figure 4:
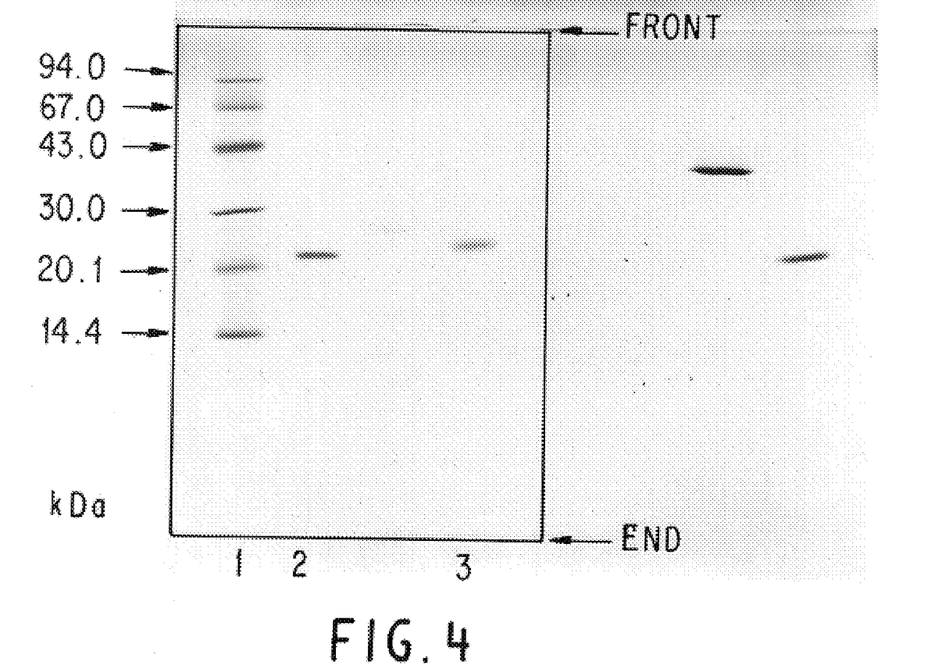
FIG. 4 shows the SDS-PAGE patterns of PEG-bonded rhIL-6.

The thus-purified, PEG-bonded rhIL-6 was analyzed through reversed-phase HPLC, and the data obtained are shown in FIG. 4. As in FIG. 4, the PEG-bonded rhIL-6 gave a single band at the position of a molecular weight of about 24,000. From this, it is presumed that one molecule of PEG bonded to the non-modified rhIL-6 to give the modified product, PEG-bonded rhIL-6.

In FIG. 4, 1 indicates rhIL-6, and 2 indicates the pure PEG-bonded rhIL-6. In this, the PEG-bonded rhIL-6 gave a single band.

EXAMPLE 5 i) in-vitro Activity of Polylysine-Bonded rhIL-6 and PEG-Bonded rhIL-6:

Method:

Used herein was MH60.32, which had been obtained through sub-cloning of IL-6-dependent mouse hybridoma MH60 BSF2.

The following solutions were put into each well of a 96-well plate.

a) 100 µl of a sample solution as stepwise diluted with a medium (starting from 100 mg/ml, the solution was stepwise diluted at intervals of 3 times).

b) $5 \times 10^3$ cells of MH60 as suspended in 100 µl of the medium (prior to being suspended, the cells were washed three time with the medium).

The cells in each well were incubated at 37° C. in 50% $CO_2$ for 60 hours, the number of the cells was counted through MTT assay. Briefly, 50 µl of a solution of MTT (3-[4,5-dimethylthiazol-2-yl]-2,5-diphenyltetrazolium bromide, 1 mg/ml, PBS solution) was added to each well, and left as it was for about 6 hours; then 150 µl of the supernatant was removed; and 100 µl of a solution for dissolving MTT (20% SDS, 0.04 N HCl solution) was added thereto and left as it was overnight. Using a micro-plate reader, the absorbance (570 to 620 nm) was measured. The medium used in this experiment was PRPMI 1640 (produced by Gibco) with 10% VCS (passivated). The units were calculated according to the Hirano et al's method (see Proc. N.A.S., 82,5490 (1985)).

Results:

As in Table 2, the three samples of polylysine-bonded rhIL-6 (as prepared in Example 3) and the sample of PEG-bonded rhIL-6 were almost comparable to the non-modified, original rhIL-6 with respect to the activity of enhancing the propagation of cells of MH60.

TABLE 2 in-vitro Activity (for enhancing the propagation of cells of MH60) of Polylysine-bonded rhIL-6 and PEG-bonded rhIL-6

| Protein | $\times 10^5$ units/nmol |
| --- | --- |
| rhIL-6 | 1.05 |
| Polylysine (MW 7,900)-bonded rhIL-6 | 1.00 |
| Polylysine (MW 45,700)-bonded rhIL-6 | 0.90 |
| Polylysine (MW 83,800)-bonded rhIL-6 | 0.85 |
| PEG-bonded rhIL-6 | 1.01 | ii) in-vivo Activity of Polylysine-Bonded rhIL-6 and PEG-Bonded rhIL-6:

Method:

Healthy, male ICR mice of about 6 week-age having a body weight of about 25 g were used herein. 0.1 ml of each sample was subcutaneously injected to each mouse. Prior to its injection, the sample was diluted with a citrate buffer (sodium citrate, pH 7.0). To the control, injected was the citrate buffer. The test animals were grouped into plural groups, one group comprised of 5 mice. The injection was effected twice a day (in the morning and in the evening), totaling 9 times in the morning on day 5. 4 to 8 hours after the final injection, the blood was collected from the heart of each test animal and then mixed with an anti-coagulant. Within 3 hours after the blood collection, the number of the platelets in the blood sample was counted according to the method of detecting the variation in the electric resistance of the sample.

Results:

As in Table 3, the significant increase in the number of platelets was obtained in the test animals to which had been administered any of the three polylysine-bonded rhIL-6 samples (as prepared in Example 3) and the PEG-bonded rhIL-6 sample, as compared with those to which had been administered the non-modified, original rhIL-6.

TABLE 3 in-vivo Activity (for increasing the number of platelets) of Polylysine-Bonded rhIL-6 and PEG-Bonded rhIL-6

| Protein | Number of Platelets (+ SD) ($\times 10^4/\mu l$) |
| --- | --- |
| Citrate Buffer (control) | 111.2 + 8.9 |
| rhIL-6 | 124.6 + 19.1 |
| Polylysine (MW 7,900)-Bonded rhIL-6 | 135.3 + 7.8 |
| Polylysine (MW 45,700)-Bonded rhIL-6 | 143.2 + 8.1 |
| Polylysine (MW 83,800)-Bonded rhIL-6 | 138.5 + 10.2 |
| PEG-Bonded rhIL-6 | 145.4 + 9.8 |

EXAMPLE 6

Bonding of Monoclonal Antibody to IL-6:

To a mouse monoclonal anti-rat megakaryocyte/platelet antibody (50 µg/50 µl, 50 mM Tris-HCl, pH 7.5), added was BTG (1U/100 µl, 50 mM Tris-HCl, pH7.5), and left at room temperature for 30 minutes. Next, rhIL-6 (50 µg/25 µl, 10 mM sodiumcitrate, pH 7.0) was added thereto, and reacted at 20° C. for 4 hours. The reaction solution was applied onto a mouse monoclonal anti-hIL-6 antibody column that had been previously equilibrated with 10 mM sodium acetate buffer (pH 7.0), and then eluted with 0.1N HCl with 2 M NaCl. The resulting eluate was diluted 3-fold with 0.3 M Tris-HCl (pH 8.5), then applied onto a Protein G column (produced by Pharmacia) that had been previously equilibrated with 10 mM sodium acetate buffer (pH 7.0), and thereafter eluted with 0.1 M glycine-HCl buffer (pH 2.7). The thus-eluted fraction was subjected to SDS-PAGE, and then subjected to Western blotting with the anti-rhIL-6 antibody.

Figure 5:
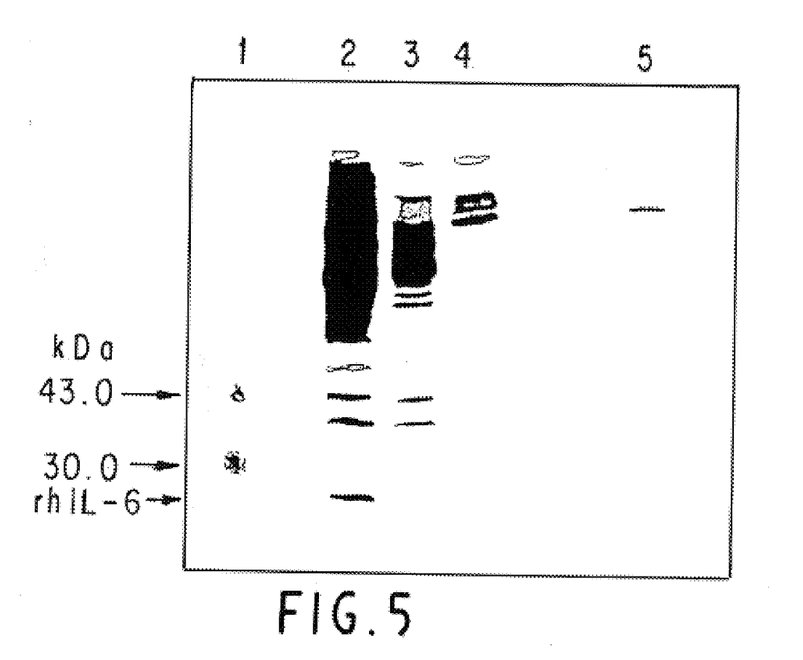
FIG. 5 shows the data obtained in Western blotting of monoclonal antibody-bonded rhIL-6.

The data are shown in FIG. 5. Both the substance as adsorbed to the anti-rhIL-6 antibody column and the substance as adsorbed to the Protein G column were detected in the polymer region, and this supports that the monoclonal antibody bonded to rhIL-6.

In FIG. 5, 1 indicates the marker; 2 indicates the reaction solution; 3 indicates the eluate from the anti-rhIL-6 antibody column; 4 indicates the fraction adsorbed to the anti-rhIL-6 antibody column; and 5 indicates the fraction adsorbed to the Protein G column. In this, the bands in the lane 3 indicate that the antibody-bonded rhIL-6 overflowed the antibody column, as exceeding the capacity of the column.

EXAMPLE 7

Preparation of Polyethylene Glycol (PEG)-Bonded rhIL-2:

A solution of rhIL-2 (2.5 ml) as dissolved in 50 mM acetate buffer containing 0.25 M NaCl (pH 5.0) was applied onto a column of "Sephadex G-25" that had been previously equilibrated with 200 mM Tris-HCl buffer (pH 7.5), and then eluted with the same Tris buffer. While monitoring the resulting eluate on the basis of its absorbance at 280 nm, an eluate fraction of rhIL-2 (3 ml) was obtained. The protein concentration in this eluate fraction of rhIL-2 was determined on the basis of its molecular extinction coefficient at 280 nm of $1.2 \times 10^4$ $M^{-1}cm^{-1}$. Then, this fraction was diluted with the above-mentioned Tris buffer to prepare a protein solution of 5 µM. To the thus-diluted protein solution (2.5 ml), added was 75 mg of bis (6-aminohexyl) polyoxyethylene (molecular weight: 3,350—produced by Sigma), and pre-incubatedat 37° C. To the resulting reaction solution, added was 250 μl of a solution of BTG (220 U/ml, 200 mM Tris-HCl buffer, pH 7.5), and incubated at 37° C. for 2 hours.

Figure 6:
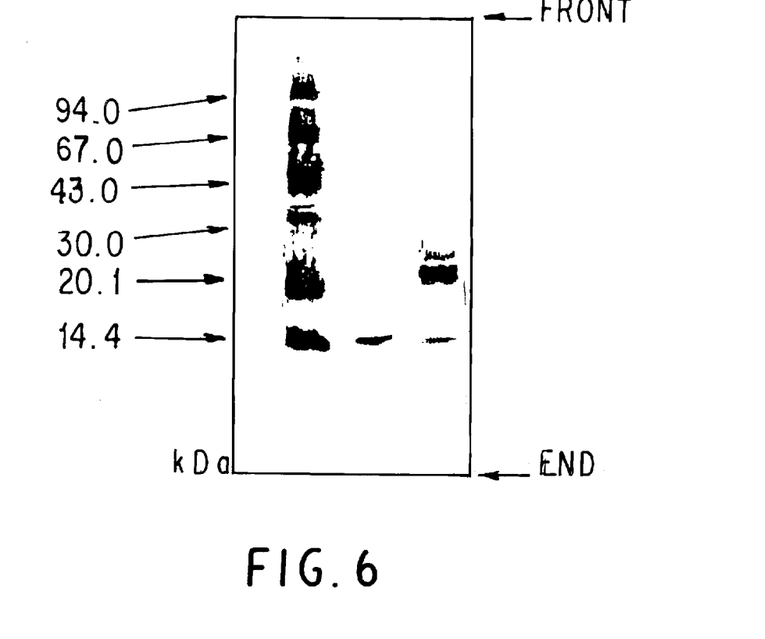
FIG. 6 shows the SDS-PAGE patterns of polyethylene glycol (PEG)-bonded rhIL-2.

The resulting reaction solution was purified through reversed-phase HPLC, using a column of "YMC C8 AP" (produced by Yamamura Chemical), thereby removing the non-reacted rhIL-2 fraction therefrom. Using Phast System (produced by Pharmacia), the purified product was then analyzed through SDS-PAGE (in which was used Homogeneous 20 Gel) to determine its purity. In this SDS-PAGE, the product as modified with PEG (PEG-rhIL-2) gave a protein-derived band only at the position that is higher than the position for the non-modified rhIL-2 by one molecule of PEG (see FIG. 6). This band suggests that the modified product comprises rhIL-2 with one molecule of PEG bonded thereto. In FIG. 6, 1 indicates the molecular weight marker; 2 indicates rhIL-2; and 3 indicates the PEG-bonded rhIL-2.

EXAMPLE 8

IL-2 Activity of Polyethylene Glycol (PEG)-Bonded rhIL-2 (PEG-rhIL-2):

IL-2-dependent mouse cells of "CTLL-2" were incubated in an RPMI 1640 medium containing 10% FCS (fetal calf serum) and containing about 50 units/ml of rat IL-2 (produced by Collaborative). The cells were suspended in an RPMI 1640 medium containing 10% FCS to give a cell suspension of $4 \times 10^4$ cells/ml, after having been washed with said medium. 100 μl of the cell suspension was pipetted into each well of a 96-well plate for tissue culture, and 100 μl of PEG-rhIL-2 or non-modified rhIL-2 that had been diluted with an RPMI 1640 medium containing 10% FCS was added to each well. Thus, the cells were incubated in each well. 20 hours after the start of the incubation, "Methyl-3H" Thymidine (740 GBq/mmol—produced by NEN), which had been diluted 100-fold with a 10% FCS-containing RPMI 1640 medium to have a concentration of 370 KBq/50 μl, was added to each well, and the cells were further incubated for 4 hours in each well. After the incubation, the radioactivity of the cells was measured, using "Matrix 96 Direct Beta Counter" (produced by Packard). As a result, the relative activity of PEG-rhIL-2, relative to the non-modified rhIL-2, was 97%, which supports that the PEG-modified product, PEG-rhIL-2 still had the IL-2 activity.

EXAMPLE 9

Preparation of Polyethylene Glycol (PEG)-Bonded rhIL-6:

A solution of rhIL-6 (1.75 mg/ml) as dissolved in 10 mM sodium citrate buffer (pH 6.0) was diluted with 200 mM Tris-HCl buffer (pH 7.5) to prepare a protein solution of 5 μM. To the thus-diluted protein solution (2.5 ml), added was 75 mg of bis(6-aminohexyl) polyoxyethylene (molecular weight: 3,350—produced by Sigma), and pre-incubated at 37° C. To the resulting reaction solution, added was 250 μl of a solution of BTG (220 U/ml, 200 mM Tris-HCl buffer, pH 7.5), and incubated at 37° C. for 2 hours.

Figure 7:
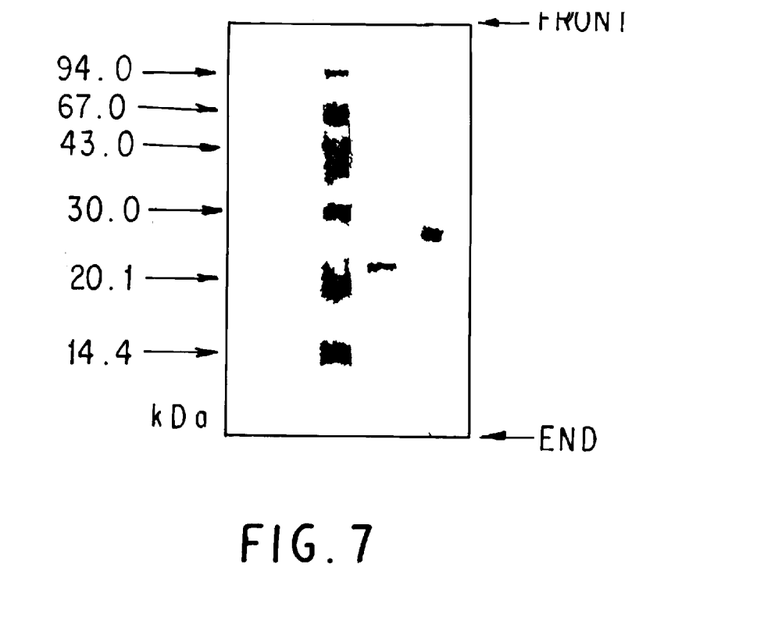
FIG. 7 shows the SDS-PAGE patterns of polyethylene glycol (PEG)-bonded rhIL-6.

The resulting reaction solution was purified through reversed-phase HPLC, using a column of "YMC C8 AP" (produced by Yamamura Chemical), thereby removing the non-reacted rhIL-6 fraction therefrom. Using Phast System (produced by Pharmacia), the purified product was then analyzed through SDS-PAGE (in which was used Homogeneous 20 Gel) to determine its purity. In this SDS-PAGE, the product as modified with PEG (PEG-rhIL-6) gave a protein-derived band only at the position that is higher than the position for the non-modified rhIL-6 by one molecule of PEG (see FIG. 7). This band suggests that the modified product comprises rhIL-6 with one molecule of PEG bonded thereto. In FIG. 7, 1 indicates the molecular weight marker; 2 indicates rhIL-6; and 3 indicates the PEG-bonded rhIL-6.

EXAMPLE 10

Preparation of Polyethylene Glycol (PEG)-Bonded rINF-α-2b:

A lyophilized product of rINF-α-2b (produced by Yamanouchi) was dissolved in 200 mM Tris-HCl buffer (pH 7.5) to prepare a protein solution of 5 μM. To the thus-prepared protein solution (2.5 ml), added was 22.5 mg of bis(6-aminohexyl) polyoxyethylene (molecular weight: 3,350—produced by Sigma), and pre-incubated at 37° C. To the resulting reaction solution, added was 250 μl of a solution of BTG (220 U/ml, 200 mM Tris-HCl buffer, pH 7.5), and incubated at 37° C. for 2 hours.

Figure 8:
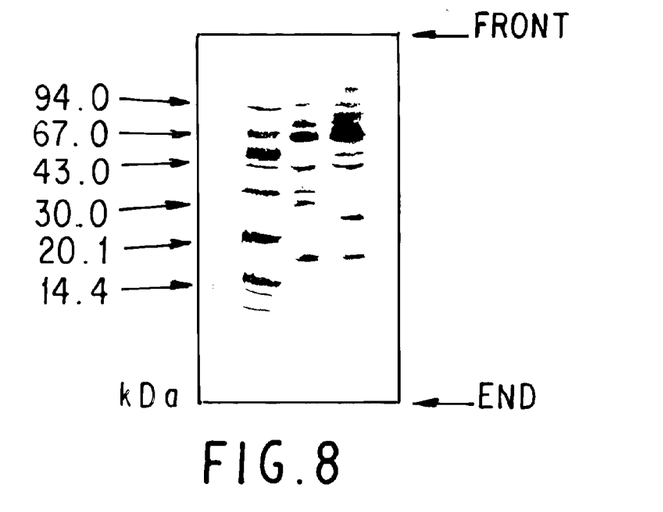
FIG. 8 shows the SDS-PAGE patterns of polyethylene glycol (PEG)-bonded rINF-α-2b.

Using Phast System (produced by Pharmacia), the resulting reaction solution was analyzed through SDS-PAGE (in which was used Homogeneous 20 Gel). In this SDS-PAGE, the product as modified with PEG (PEG-rINF-α-2b) gave a protein-derived band only at the position that is higher than the position for the non-modified rINF-α-2b by one molecule of PEG (see FIG. 8). This band suggests that the modified product comprises rINF-α-2b with one molecule of PEG bonded thereto. In FIG. 8, 1 indicates the molecular weight marker; 2 indicates rINF-(α-2b; and 3 indicates the PEG-modified reaction solution. In this, the spot for about 43.0 KDa in the lane 3 indicates BTG in the reaction solution; and the spots for 67.0 KDa or larger in the lane 3 indicate human serum albumin (HSA) in the non-modified rINF-α-2b.

EXAMPLE 11

Preparation of Polyethylene Glycol (PEG)-Bonded rADF:

A lyophilized product of rADF was dissolved in 200 mM Tris-HCl buffer (pH 7.5) to prepare a protein solution of 5 μM. To the thus-prepared protein solution (2.5 ml), added was 22.5 mg of bis(6-aminohexyl) polyoxyethylene (molecular weight: 3,350—produced by Sigma), and pre-incubated at 37° C. To the resulting reaction solution, added was 250 μl of a solution of BTG (220 U/ml, 200 mM Tris-HCl buffer, pH 7.5), and incubated at 37° C. for 2 hours.

Figure 9:
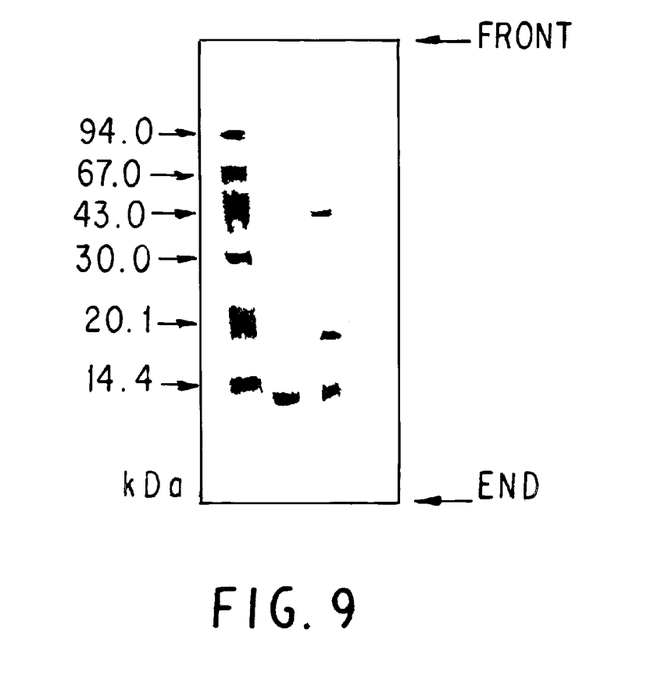
FIG. 9 shows the SDS-PAGE patterns of polyethylene glycol (PEG)-bonded rADF.

Using Phast System (produced by Pharmacia), the resulting reaction solution was analyzed through SDS-PAGE (in which was used Homogeneous 20 Gel). In this SDS-PAGE, the product as modified with PEG (PEG-rADF) gave a protein-derived band only at the position that is higher than the position for the non-modified rADF by one molecule of PEG (see FIG. 9). This band suggests that the modified product comprises rADF with one molecule of PEG bonded thereto. In FIG. 9, 1 indicates the molecular weight marker; 2 indicates rADF; and 3 indicates the PEG-modified reaction solution. In this, the spot for about 43.0 KDa in the lane 3 indicates BTG in the reaction solution.

We claim:

1. A process for modifying a biologically-active peptide or protein, comprising reacting a biologically-active peptide or protein having at least one glutamine residue with a substance having an amino donor in the presence of a transglutaminase originating in a microorganism, to form an acid-amide linkage between the γ-positioned acid amide of the glutamine residue and the amino group of the amino donor,     wherein the substance having an amino donor is selected from the group consisting of monoclonal antibodies and alkylamine derivatives of polyethyleneglycol.

2. The process according to claim 1, wherein the biologically-active protein having a glutamine residue is selected from the group consisting of IL-2, IL-6, interferon and ATL derived factor (ADF).

3. The process according to claim 1, wherein the substance having an amine donor is a monoclonal antibody.

4. The process according to claim 1, wherein the substance having an amine donor is a monoclonal antibody and the biologically-active peptide or protein is IL-2.

5. The process according to claim 1, wherein the substance having an amine donor is an alkylamine derivative of polyethyleneglycol.

6. A process for modifying IL-2, comprising reacting IL-2 with a substance having an amino donor in the presence of a transglutaminase originating in a microorganism, to form an acid-amide linkage between the γ-positioned acid amide of the glutamine residue and the amino group of the amino donor, wherein the substance having an amino donor is selected from the group consisting of polylysine, monoclonal antibodies and alkylamine derivatives of polyethyleneglycol.

7. The process of claim 6, wherein the substance having an amino donor is polylysine.

8. The process of claim 6, wherein the substance having an amino donor is a monoclonal antibody.

9. The process of claim 6, wherein the substance having an amino donor is an alkylamine derivative of polyethyleneglycol.

10. A process for modifying a biologically-active peptide or protein, comprising reacting a biologically-active peptide or protein having at least one glutamine residue with a substance having an amino donor in the presence of a transglutaminase originating in a microorganism, to form an acid-amide linkage between the γ-positioned acid amide of the glutamine residue and the amino group of the amino donor, wherein the substance having an amino donor is selected from the group consisting of polylysine, monoclonal antibodies and alkylamine derivatives of polyethyleneglycol, and the a biologically-active peptide or protein is selected from the group consisting of interleukin-2, interleukin-6, interferons, and ATL derived factor.

* * * * *